United States Patent
Garbe et al.

(10) Patent No.: US 9,908,904 B2
(45) Date of Patent: Mar. 6, 2018

(54) TRIORGANOBORANE-AMINO FUNCTIONALIZED NANOPARTICLES, COMPOSITIONS, AND METHODS

(71) Applicant: 3M INNOVATIVE PROPERTIES COMPANY, St. Paul, MN (US)

(72) Inventors: James E. Garbe, Stillwater, MN (US); Jimmie R. Baran, Jr., Prescott, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 128 days.

(21) Appl. No.: 14/652,462

(22) PCT Filed: Dec. 11, 2013

(86) PCT No.: PCT/US2013/074257
§ 371 (c)(1),
(2) Date: Jun. 16, 2015

(87) PCT Pub. No.: WO2014/099516
PCT Pub. Date: Jun. 26, 2014

(65) Prior Publication Data
US 2015/0353587 A1    Dec. 10, 2015

Related U.S. Application Data

(60) Provisional application No. 61/739,856, filed on Dec. 20, 2012.

(51) Int. Cl.
| | | |
|---|---|---|
| *C01B 35/14* | (2006.01) | |
| *B32B 5/16* | (2006.01) | |
| *C07F 7/18* | (2006.01) | |
| *C08F 120/14* | (2006.01) | |
| *C08F 120/68* | (2006.01) | |
| *C08F 120/12* | (2006.01) | |
| *C09C 1/36* | (2006.01) | |
| *C09C 3/08* | (2006.01) | |
| *C09C 3/12* | (2006.01) | |
| *C09C 1/30* | (2006.01) | |
| *B82Y 30/00* | (2011.01) | |

(52) U.S. Cl.
CPC ............ *C07F 7/1836* (2013.01); *B82Y 30/00* (2013.01); *C01B 35/146* (2013.01); *C08F 120/12* (2013.01); *C08F 120/14* (2013.01); *C08F 120/68* (2013.01); *C09C 1/3081* (2013.01); *C09C 1/3684* (2013.01); *C09C 3/08* (2013.01); *C09C 3/12* (2013.01); *C01P 2004/64* (2013.01); *Y10T 428/2982* (2015.01)

(58) Field of Classification Search
CPC .................................................. C01B 35/146
USPC .............................................. 428/403, 407
See application file for complete search history.

(56) References Cited

U.S. PATENT DOCUMENTS

| | | | |
|---|---|---|---|
| 4,356,296 A | 10/1982 | Griffith | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,752,338 A | 6/1988 | Reiners | |
| 5,026,902 A | 6/1991 | Fock | |
| 5,076,844 A | 12/1991 | Fock | |
| 5,539,070 A | 7/1996 | Zharov | |
| 5,621,143 A | 4/1997 | Pocius | |
| 5,686,544 A | 11/1997 | Pocius | |
| 5,872,197 A | 2/1999 | Deviny | |
| 6,740,716 B2 | 5/2004 | Webb | |
| 6,812,308 B2 | 11/2004 | Deviny | |
| 7,241,437 B2 | 7/2007 | Davidson | |
| 7,649,068 B2 | 1/2010 | Ahn | |
| 7,732,543 B2 | 6/2010 | Loch | |
| 8,119,245 B2 | 2/2012 | Kendi | |
| 2006/0122319 A1* | 6/2006 | Kneafsey | .............. C08F 2/38 524/556 |
| 2007/0135601 A1 | 6/2007 | Diakoumakos | |
| 2008/0085983 A1* | 4/2008 | Ahn | ............... C08F 220/18 528/5 |
| 2009/0247720 A1 | 10/2009 | Wang | |
| 2010/0221429 A1* | 9/2010 | Ahn | ................... B41M 1/06 427/256 |

FOREIGN PATENT DOCUMENTS

| | | |
|---|---|---|
| WO | WO 1997-07171 | 2/1997 |
| WO | WO 2000-38619 | 7/2000 |
| WO | WO 2000-42092 | 7/2000 |
| WO | WO 2001-07444 | 2/2001 |
| WO | WO 2001-92271 | 12/2001 |
| WO | WO 2006-049792 | 5/2006 |
| WO | WO 2006-088571 | 8/2006 |
| WO | WO 2009-085926 | 7/2009 |

OTHER PUBLICATIONS

Meliorum Technologies, Silicon Nanomaterial Datasheet, 2003.*
U.S. Research Nanomaterials, Inc., The Test Report of Silicon Nanoparticles, 2009.*
Sonnenshein, "Physical and Chemical Probes of the Bond Strength between Trialkylboranes and Amines and Their Utility as Stabilized Free Radical Polymerization Catalysts," Macromolecules, 2006, vol. 39, pp. 2507-2513.
Welch, "Polymerization of Methyl Methacrylate by Triethylboron-Oxygen Mixtures," Journal of Polymer Science, 1962, vol. 61, pp. 243-252.
International Search Report for PCT International Application No. PCT/US2013/074257 dated Mar. 12, 2014, 4 pages.

* cited by examiner

*Primary Examiner* — Hoa T Le
(74) *Attorney, Agent, or Firm* — Adrian L. Pishko

(57) ABSTRACT

Surface-modified nanoparticles wherein each nanoparticle includes an inorganic core and surface modifying groups, wherein the surface modifying groups include at least one triorganoborane-amine complex having the structure —Z—NHR$^1$—B(R$^2$)$_3$ wherein: Z is a divalent organic group; R$^1$ is H or an organic group; and each R$^2$ is independently an organic group bound to the boron atom through a carbon atom. The inorganic core is typically an inorganic oxide core, e.g., silica, zirconia, or alumina.

17 Claims, No Drawings

TRIORGANOBORANE-AMINO FUNCTIONALIZED NANOPARTICLES, COMPOSITIONS, AND METHODS

CROSS REFERENCE TO RELATED APPLICATIONS

This application is a national stage filing under 35 U.S.C. 371 of PCT/US2013/074257, filed Dec. 11, 2013, which claims priority to U.S. Application No. 61/739,856, filed Dec. 20, 2012, the disclosure of which is incorporated by reference in its/their entirety herein.

BACKGROUND

Small molecule Lewis acid/base complexes of organoboranes and amines are known. They can be formed by the reaction of a triorganoborane (a Lewis acid) and an amine (a Lewis base). Amines that form the most stable complexes with triorganoboranes include primary amines and some secondary amines. Tertiary amines, sterically hindered secondary amines, and amines in which the nitrogen atom lone electron pair is delocalized (and thus not available to form a strong dative bond with the boron atom via the boron empty p orbital) form less stable complexes with organoboranes. The complexes have the general structure

wherein each R is independently an alkyl group, a cycloalkyl group, or an aralkyl group, and each $R^1$ is independently H, an alkyl group, or a cycloalkyl group.

The triorganoborane-amine complexes can be "decomplexed" by compounds that react with amines, thereby liberating free triorganoborane. This reaction is typically irreversible such that the amine is then no longer available to complex the triorganoborane. The free triorganoborane can react with oxygen to generate several free-radical species, some of which are known to initiate radical polymerization of unsaturated monomers, such as acrylates.

While such conventional triorganoborane-amine complexes are more stable than the free triorganoborane with respect to oxidation by atmospheric oxygen, there is still a need for even greater stability. Furthermore, such conventional triorganoborane-amine complexes are liquids often kept under an inert atmosphere, and thus are not easily stored, transported, or handled.

SUMMARY

The present disclosure provides triorganoborane-amine functionalized nanoparticles that are generally more easily stored, transported, and handled than liquid borane-amine complexes. Such functionalized nanoparticles can be delivered and subsequently decomplexed, releasing the active species, a triorganoborane, for its intended use. Significantly, the triorganoborane can be liberated from the nanoparticles by treating the functionalized nanoparticles with, for example, a decomplexing agent such as carboxylic acid. The liberated triorganoborane is capable of being used, for example, as an initiator for polymerization reactions, such as for free radical polymerization reactions of ethylenically unsaturated monomers (e.g., acrylate monomers).

In one embodiment, the present disclosure provides a surface-modified nanoparticle that includes an inorganic core and surface modifying groups, wherein the surface modifying groups include at least one triorganoborane-amine complex having the structure —Z—NHR$^1$—B(R$^2$)$_3$ wherein: Z is a divalent organic group; $R^1$ is H or an organic group; and each $R^2$ is independently an organic group bound to the boron atom through a carbon atom. The inorganic core is typically an inorganic oxide core, e.g., silica, zirconia, or alumina.

In one embodiment, the present disclosure provides a dispersion of a plurality of such surface-modified nanoparticles in a liquid.

In one embodiment, a method of making surface-modified nanoparticles is provided, wherein the method includes: providing amine-functional inorganic nanoparticles including bound stabilizing organic groups selected to stabilize a plurality of the nanoparticles when dispersed in a liquid; providing a triorganoborane compound of the formula B(R$^2$)$_3$ wherein each $R^2$ is independently an organic group bound to the boron atom through a carbon atom; and combining the amine-functional inorganic nanoparticles and the triorganoborane compound under conditions effective to form surface-modified nanoparticles. Each surface-modified nanoparticle includes an inorganic core and surface modifying groups, wherein the surface modifying groups include at least one triorganoborane-amine complex having the structure —Z—NHR$^1$—B(R$^2$)$_3$ wherein: Z is a divalent organic group; $R^1$ is H or an organic group; and each $R^2$ is independently an organic group bound to the boron atom through a carbon atom.

In one embodiment, a polymerizable composition is provided that includes a polymerizable component and surface-modified nanoparticles as described herein.

The term "nanoparticle" refers to a particle having a particle size (i.e., the longest dimension of a particle, for example, the diameter of a sphere) of no greater than 100 nanometers (nm), which is a nonagglomerated and nonaggregated discrete particle, as well as agglomerated or aggregated particles having a particle size (i.e., the longest dimension of an agglomerate or aggregate, for example, the diameter of a sphere) of no greater than 100 nanometers (nm). The term "nanoparticle" herein excludes fumed or pyrogenic inorganic oxides (such as fumed silica (which is also sometimes referred to as precipitated silica), pyrogenic, silica, or fumed alumina).

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). In the context of the present invention, the organic groups are those that do not interfere with the formation of an organoborane-amine complex and/or monomer polymerization or ethylenically unsaturated monomers. The term "aliphatic group" means a saturated or unsaturated linear or branched hydrocarbon group. This term is used to encompass alkyl, alkenyl, and alkynyl groups, for example. The term "alkyl group" is defined below. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" is defined below. The term "heterocyclic group" means a closed ring hydrocarbon in which one or more of the atoms in the ring is an element other than carbon (e.g., nitrogen, oxygen, sulfur, etc.). Unless otherwise indicated, the organic groups typically contain at least 1 carbon atom, and often up to 30 carbon atoms. The organic group can have any suitable valency but is often monovalent or divalent.

The term "alkyl" refers to a monovalent group that is a radical of an alkane and includes straight-chain, branched, cyclic, and bicyclic alkyl groups, and combinations thereof, including both unsubstituted and substituted alkyl groups. Unless otherwise indicated, the alkyl groups typically contain from 1 to 30 carbon atoms. In some embodiments, the alkyl group contains 1 to 20 carbon atoms, 1 to 10 carbon atoms, 1 to 6 carbon atoms, 1 to 4 carbon atoms, or 1 to 3 carbon atoms. Examples of alkyl as used herein includes, but are not limited to, methyl, ethyl, n-propyl, n-butyl, n-pentyl, isobutyl, t-butyl, isopropyl, n-octyl, n-heptyl, ethylhexyl, and the like.

The term "cycloalkyl" refers to a closed ring alkyl group. Unless otherwise indicated, the cycloalkyl group typically has 1 to 30 carbon atoms. Examples of cycloalkyl groups include but are not limited to, cyclopentyl, cyclohexyl, cycloheptyl, adamantyl, norbornyl, and the like.

The term "alkylene group" refers to a divalent group that is a radical of an alkane and includes straight-chain, branched, and cyclic groups, and combinations thereof, include both unsubstituted and substituted alkylene groups. Unless otherwise indicated, the alkylene group typically has 1 to 20 carbon atoms, 1 to 10 carbon atoms, 1 to 6 carbon atoms, or 1 to 4 carbon atoms.

The term "aryl" refers to a monovalent group that is aromatic and optionally carbocyclic. The aryl has at least one aromatic ring and can have one or more additional carbocyclic rings that are fused to the aromatic ring. Any additional rings can be unsaturated, partially saturated, saturated, or aromatic, Unless otherwise indicated, the aryl groups typically contain from 6 to 30 carbon atoms. In some embodiments, the an groups contain 6 to 20, 6 to 18, 6 to 16, 6 to 12, or 6 to 10 carbon atoms. Examples of an aryl group include phenyl, naphthyl, biphenyl, phenanthryl, and anthracyl.

The term "aralkyl" refers to a monovalent group that is an alkyl group substituted with an aryl group. The term "alkaryl" refers to a monovalent group that is an aryl substituted with an alkyl group. For both groups, the alkyl portion often has 1 to 10 carbon atoms, 1 to 6 carbon atoms, or 1 to 4 carbon atoms and an aryl portion often has 6 to 20 carbon atoms, 6 to 18 carbon atoms, 6 to 16 carbon atoms, 6 to 12 carbon atoms, or 6 to 10 carbon atoms.

The term "hydrolyzable" refers to a group that can react with water having a pH of 1 to 10 under conditions of atmospheric pressure. The hydrolyzable group is often converted to a hydroxyl group when it reacts. The hydroxyl group often undergoes further reactions. Typical hydrolyzable groups include, but are not limited to, alkoxy, aryloxy, aralkyloxy, alkaryloxy, acyloxy, or halo. As used herein, the term is often used in reference to one or more groups bound to a silicon atom in a silyl group.

The term "non-hydrolyzable group" refers to a group that cannot react with water having a pH of 1 to 10 under conditions of atmospheric pressure. Typical non-hydrolyzable groups include, but are not limited to, alkyl, aryl, aralkyl, and alkaryl. As used herein, the term is often used in reference to one or more groups bonded to a silicon atom in a silyl group.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term at least one. The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein, in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

A group that may be the same or different is referred to as being "independently" something. That is, when a group is present more than once in a formula described herein, each group is independently selected, whether specifically stated or not. For example, when more than one $R^2$ group is present in a formula, each $R^2$ group is independently selected. Furthermore, subgroups contained within these groups are also independently selected.

As used herein, the term "room temperature" refers to a temperature of 20° C. to 25° C. or 22° C. to 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF EXEMPLARY EMBODIMENTS

The present disclosure provides surface-modified nanoparticles that include one or more triorganoborane-amine complexes. In one embodiment, the surface-modified nanoparticles include an inorganic core and surface modifying groups, wherein the surface modifying groups include at least one triorganoborane-amine complex having the structure $-Z-NHR^1-B(R^2)_3$ wherein: Z is a divalent organic group; $R^1$ is H or an organic group; and each $R^2$ is independently an organic group bound to the boron atom through a carbon atom.

In certain embodiments, such surface-modified nanoparticles are the reaction product of a triorganoborane and an amine-functional nanoparticle (e.g., an amine-functional nanosilica particle). The nanoparticles include bound Lewis acid-base complexes of triorganoborane and amine-functional organic groups. These radical precursor complexes that are tethered to a nanoparticle can function as a source of free radicals. Furthermore, such surface-modified nanoparticles can also function as reinforcing fillers in polymerizable systems such as curable adhesives and other curable multi-part formulations. Thus, these solid, dispersible, free-radical sources are useful as free-radical polymerization initiators, and can be used to prepare a 2-part dual-cure system. Because the Lewis-acid base complex is in a solid form, the amount of such complex can be more easily delivered and the amount delivered more controllable compared to a complex that is in a liquid form.

In certain embodiments, the structure of the surface-modified nanoparticle complexes with the tethered (i.e., bound) complexes of triorganoborane and amine-functional organic groups can be represented by the following structure:

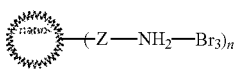

where Z is a divalent organic group having at least 1 carbon atom, each R is independently an alkyl, cycloalkyl, or arylalkyl group, and n is an integer of at least 1. The nanoparticle, represented by the circle, can be any type of inorganic nanoparticle but is typically an inorganic oxide nanoparticle.

Significantly, the present disclosure presents nanoparticles that have been selectively surface modified in such a way as to form complexes with, and thereby de-activate or stabilize, active chemical species. Once formed, these nanoparticle complexes can be more easily delivered, used, and stored until the complex is subsequently decomposed, thereby releasing the active species for its intended use.

More specifically, the surface-modified nanoparticles of the present disclosure are stable to oxidation by atmospheric oxygen, and they provide at least the following features: 1) they are a convenient solid source of triorganoboranes for radical reactions such as polymerization of ethylenically unsaturated monomers, 2) they have utility as reinforcing fillers in polymerizable systems, and 3) the triorganoboranes bound to the nanoparticles are "diluted" by the inorganic nanoparticles (e.g., inorganic oxide), a non-combustible carrier for the triorganoboranes.

Free triorganoborane can be liberated from the nanoparticles by treating the surface-modified nanoparticles with, for example, a decomplexing agent. Typically, the decomplexing agent is an amine-reactive compound that can react with the amine group of the amine-functional nanoparticle. Useful decomplexing agents include isocyanates, and acids (including carboxylic acids, and carboxylic acid anhydrides). Useful isocyanates can include, e.g., phenyl isocyanate, toluene diisocyanate, and polyisocyanates such as those available from Bayer MaterialScience, Pittsburgh, Pa., under the trade designations DESMODUR N100 and DESMODUR N3300. Useful acids include mineral acids such as hydrochloric acid and sulfuric acid, carboxylic acids, including mono-, di-, and polycarboxylic acids such as acetic acid, propionic acid, oxalic acid, succinic acid, maleic acid, acrylic acid, and methacrylic acid, and sulfonic acids such as benzenesulfonic acid and toluenesulfonic acid. Useful carboxylic anhydrides include succinic anhydride, malic anhydride, acrylic anhydride, and itaconic anhydride. Useful decomplexing agents are described in, for example, U.S. Pat. No. 5,686,544 (Pocius), WO 97/07171 (Deviny), U.S. Pat. No. 5,872,197 (Deviny), and U.S. Pat. No. 6,812,308 (Deviny et al.). The liberated triorganoborane is capable of initiating the polymerization of acrylate monomers, for example.

Nanoparticles

Nanoparticles of the present disclosure include an inorganic core, particularly an inorganic oxide core (e.g., zirconia, titania, silica, ceria, alumina, iron oxide, vanadia, germanium oxide, zinc oxide, antimony oxide, tin oxide, and alumina-silica). In some embodiments, the nanoparticles include silica, zirconia, or mixtures thereof.

The nanoparticle can include an oxide of a non-metal, an oxide of a metal, or combinations thereof. An oxide of a non-metal includes an oxide of, for example, silicon or germanium. An oxide of a metal includes an oxide of, for example, iron, titanium, cerium, vanadium, antimony, tin, aluminum, or zirconium.

The nanoparticle can have an average particle size of no greater than 100 nanometers (nm), no greater than 75 nanometers, no greater than 50 nanometers, no greater than 25 nanometers, no greater than 20 nanometers, no greater than 15 nanometers, or no greater than 10 nanometers. The nanoparticle can have an average particle size of at least 1 nanometer, at least 5 nanometers, at least 15 nanometers, at least 20 nanometers, at least 25 nanometers, at least 50 nanometers, or at least 75 nanometers.

Various nanoparticles are commercially available. Commercial sources of nanoparticles are available from Nyacol Co. (Ashland, Mass.), Solvay-Rhodia (Lyon, France), and Nalco Co. (Naperville, Ill.). Nanoparticles can also be made using techniques known in the art. For example, zirconia nanoparticles can be prepared using hydrothermal technology as described, for example, in PCT Publication No. WO 2009/085926 (Kolb et al.).

Preferably, the inorganic (non-surface-modified) nanoparticles can be silica nanoparticles that are provided in an aqueous or in a water/organic solvent mixture having an average particle diameter of 4.0 nanometers or less, preferably 20 nanometers or less, and more preferably 10 nanometers or less. The average particle size may be determined using transmission electron microscopy.

In some embodiments, the (non-surface-modified) nanoparticles may be in the form of a colloidal dispersion. Colloidal silica nanoparticles in aqueous media are well known in the art and available commercially. Silica sols in water or water-alcohol solutions are available commercially under such trade names as LUDOX (available from Sigma-Aldrich Corp., St. Louis, Mo.), NYACOL (available from Nyacol Co., Ashland, Mass.), and NALCO (available from Nalco Co., Naperville, Ill.).

One useful silica sol is NALCO 2326 available as a silica sol with mean particle size of 5 nanometers, 10.5, and solid content 15% by weight, available from Nalco Co., Naperville, Ill. Other commercially available silica nanoparticles include NALCO 1115, NALCO 1130, NALCO 1040, NALCO 1050, NALCO 1060, NALCO 2327, and NALCO 2329 available from Nalco Co., REMASOL SP30, commercially available from Remet Corp., and LUDOX SM, commercially available from Sigma-Aldrich.

Zirconia nanoparticle dispersions are available from Nalco Chemical Co. under the trade designation NALCO OOSSOO8 and from Buhler AG, Uzwil, Switzerland under the trade designation BUHLER ZIRCONIA Z-WO. Suitable zirconia nanoparticles are also those described in, for example, U.S. Pat. No. 7,241,437 (Davidson, et al).

The nanoparticles may be fully condensed. Fully condensed nanoparticles (with the exception of amorphous silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g., zirconia) nanoparticles have a high refractive index whereas amorphous nanoparticles typically have a lower refractive index.

In certain embodiments, the inorganic core can be an inorganic oxide core, such as silica, zirconia, or alumina.

Bound Triorganoborane-Amine Complexes

The surface modifying groups include at least one triorganoborane-amine complex having the structure —Z—NHR$^1$—B(R$^2$)$_3$. Such bound (i.e., tethered) complexes are free-radical precursor complexes. The surface modifying groups are often covalently bound to the inorganic nanoparticle through an attachment group. That is, the attachment group is covalently linked to both the surface of the inorganic nanoparticle and to the surface modifying group.

In such bound complexes, Z is a divalent organic group. In certain embodiments, Z is a divalent organic group having 1 to 30 carbon atoms. In certain embodiments, Z is a divalent organic group having 1 to 20 carbon atoms. In certain embodiments, Z is a divalent organic group having 1 to 10 carbon atoms. In certain embodiments, Z is a divalent organic group having 1 to 6 carbon atoms. In certain embodiments, Z is a divalent organic group having 1 to 3 carbon atoms. In certain embodiments, Z is an alkylene group.

In such bound complexes, the R$^1$ and R$^2$ groups are selected such that a Lewis acid-base triorganoborane-amine complex readily forms between bound amine groups and a triorganoborane compound. This includes selecting such groups based on electronic and steric considerations. For example, it is desirable that R$^1$ not be too sterically hindering, or too electron withdrawing such that a Lewis acid-base complex would not form.

In such bound complexes, R$^1$ is H or an organic group. In certain embodiments, R$^1$ is H, an alkyl group, an aryl group, a cycloalkyl group, or a combination thereof (e.g., an aralkyl, an alkaryl, or an alkyl substituted with a cycloalkyl). In certain embodiments, R$^1$ is methyl, ethyl, n-propyl, —CH$_2$-phenyl, or —CH$_2$-cyclohexyl. In certain embodiments, R$^1$ is H, an alkyl group, or a cycloalkyl group. In certain embodiments, R$^1$ is H, a (C1-C6)alkyl group, or a (C4-C8)cycloalkyl group. In certain embodiments, R$^1$ is H.

Preferred R$^1$ groups are not too sterically hindering such that a Lewis acid-base complex would not form. Sterically hindered groups such as phenyl, isopropyl, t-butyl, and cyclohexyl are not desirable, although if such bulky groups are not directly bonded to the nitrogen atom of the amine group, they can be used. Examples of such groups include —CH$_2$-phenyl or —CH$_2$— cyclohexyl. Even more preferred R$^1$ groups are methyl, ethyl, and propyl groups, as these allow for more facile formation of a Lewis acid-base complex.

In such bound complexes, each R$^2$ is independently an organic group bound to the boron atom through a carbon atom. In certain embodiments, each R$^2$ is independently an alkyl group, an aryl group, a cycloalkyl group, or a combination thereof (e.g., an aralkyl group, or an alkaryl group). In certain embodiments, each R$^2$ is independently an alkyl group, a cycloalkyl group, an aralkyl group, or an alkaryl group. In certain embodiments, each R$^2$ is independently a (C1-C20)alkyl group, a (C4-C8)cycloalkyl group, a (C6-C14)ar(C1-C10)alkyl group, or a (C1-C10)alk(C6-C14)aryl group. In certain embodiments, each R$^2$ group is an alkyl group having 1 to 10 carbon atoms, 1 to 6 carbon atoms, or 1 to 4 carbon atoms. In certain embodiments, each R$^2$ is independently an alkyl group or a cycloalkyl group. In certain embodiments, each R$^2$ is independently a (C1-C20) alkyl group, a (C4-C8)cycloalkyl group. In certain embodiments, each R$^2$ is the same in the structure —Z—NHR$^1$—B(R$^2$)$_3$.

Preferred R$^2$ groups are not too electron donating such that a Lewis acid-base complex would not form. Typically, electron donating groups such as aryl groups are not as desirable as alkyl and cycloalkyl groups, although if such groups are not directly bonded to the boron atom of the triorganonoborane group, they can be used.

In certain embodiments of the triorganoborane-amine complex having the structure —Z—NHR$^1$—B(R$^2$)$_3$, Z is a divalent organic group having 1 to 30 carbon atoms; R$^1$ is H, an alkyl group, or a cycloalkyl group; and each R$^2$ is independently an alkyl group, a cycloalkyl group, an aralkyl group, or an alkaryl group.

In certain embodiments of the triorganoborane-amine complex having the structure —Z—NHR$^1$—B(R$^2$)$_3$, Z is a divalent organic group having 1 to 20 carbon atoms; R$^1$ is H or a (C1-C6)alkyl group or a (C4-C8)cycloalkyl group; and each R$^2$ is independently a (C1-C20)alkyl group, a (C4-C8) cycloalkyl group, a (C6-C14)ar(C1-C10)alkyl group, or a (C1-C10)alk(C6-C14)aryl group.

In certain embodiments of the triorganoborane-amine complex having the structure —Z—NHR$^1$—B(R$^2$)$_3$, Z is a divalent organic group having 1 to 3 carbon atoms; R$^1$ is H; and each R$^2$ is independently a (C1-C6)alkyl group.

In certain embodiments, the amine-functional organic groups can be covalently bound to inorganic oxide nanoparticles through an attachment group containing a —Si—O—Si— linkage.

Optional Groups Bound to Nanoparticles

The nanoparticles may include surface modifying groups other than the triorganoborane-amine complex having the structure —Z—NHR$^1$—B(R$^2$)$_3$. For example, the nanoparticles may further include amine-functional organic groups directly bound to the nanoparticles. By this it is meant that such amine-functional organic groups are not complexed with a triorganoborane. Such amine-functional organic groups are typically the excess groups on the amine-functional nanoparticles that are not bound to a triorganoborane.

Also, the nanoparticles may include additional stabilizing (typically, non-amine-functional) organic groups directly bound to the nanoparticles. Such organic groups are separate and distinct from (i.e., not part of) the triorganoborane-amine complexes and any amine-functional organic groups that may be bound to the nanoparticles. The additional stabilizing organic groups can be selected from a wide variety of conventional functional groups bound to nanoparticles. Typically, they are selected to stabilize a plurality of the amine-functional inorganic nanoparticles when dispersed in a liquid (e.g., water, alcohols (e.g., methanol, ethanol, 1-methoxy-2-propanol, or glycols), or combinations thereof) before complexing the bound amine-functional organic groups with a triorganoborane. Such additional stabilizing (typically, non-amine-functional) organic groups include (C1-C30)organic groups optionally containing catenary oxygen atoms and other functional groups (e.g., OH groups). In certain embodiments, the additional stabilizing organic groups include a (C3-C16)alkyl group, a (C6-C14)aryl group, or combinations thereof (alkaryl or aralkyl groups). In certain embodiments, the additional stabilizing organic group is a (C3-C16)alkyl group.

The amine-functional organic groups and the additional stabilizing organic groups can be covalently bound to inorganic oxide nanoparticles through an attachment group containing a —Si—O—Si— linkage.

Thus, in certain embodiments, the amine-functional organic groups are provided by a compound of the formula A-ZNHR$^1$, wherein A is a group that reacts with the surface of the nanoparticle to attach the group —ZNHR$^1$ to the surface, wherein Z and R$^1$ are as defined herein for —Z—NHR$^1$—B(R$^2$)$_3$. The A group can be a hydrolyzable silyl group such as a group of formula —Si(R$^3$)(R$^4$)$_2$ where R$^3$ is a hydrolyzable group and R$^4$ is a hydrolyzable group or a non-hydrolyzable group. In many embodiments, the A group is a tri(alkoxy)silyl group such as a trimethoxysilyl group or triethoxysilyl group. Exemplary compounds of the formula A-ZNHR$^1$ include, for example, 3-aminopropyltrimethoxysilane, and N-phenyl-3-aminopropyltrimethoxysilane, 3-aminopropyltriethoxysilane, 3-aminopropyldiethoxymethylsilane, 3-aminopropyldimethylethoxysilane, m-aminophenyltrimethoxysilane, p-aminophenyltrimethoxysilane, and 11-aminoundecyltriethoxysilane.

In certain embodiments, the additional stabilizing organic groups are provided by a compound of the formula A-Q, wherein A is the same as above and Q is the stabilizing organic group. In certain embodiments, Q is a (C1-C30) organic group optionally containing catenary oxygen atoms and other functional groups (e.g., OH groups). In certain embodiments, Q is a (C3-C16)alkyl group, a (C6-C14)aryl group, or combinations thereof (alkaryl or aralkyl groups). Preferred Q groups are (C3-C16)alkyl groups such as methyl, ethyl, branched and unbranched propyl, butyl, pentyl, hexyl, heptyl, octyl, nonyl, decyl, undecyl, dodecyl, tridecyl, tetradecyl, pentadecyl, and hexadecyl groups or (C6-C14)aryl groups such as phenyl groups.

Exemplary compounds of the formula A-Q include, for example, isooctyltrimethoxysilane, n-hexadecyltrimethoxysilane, phenyltrimethoxysilane, n-octyltrimethoxysilane, n-octyltriethoxysilane, dodecyltrimethoxysilane, octadecyltrimethoxysilane, n-propyltrimethoxysilane, hexyltrimethoxysilane, methyltrimethoxysilane, methyltriethoxysilane, ethyltrimethoxysilane, ethyltriethoxysilane, isopropyltrimethoxysilane, isopropyltriethoxysilane, butyltrimethoxysilane, and butyltriethoxysilane.

Methods of Making

The surface-modified nanoparticles of the present disclosure can be made by a method that includes starting with amine-functional inorganic nanoparticles that include organic groups selected to stabilize a plurality of the amine-functional inorganic nanoparticles when dispersed in a liquid (e.g., water, alcohols (e.g., methanol, ethanol, 1-methoxy-2-propanol, or glycols), or combinations thereof) before complexing the amine-functional organic groups (bound to the nanoparticles) with a triorganoborane (B(R$^2$)$_3$).

In this context, "stabilize" and "stabilizing" is defined as reducing the tendency of, and preferably preventing, said dispersion from gelling (changing from transparent or slightly hazy, such that it can be seen through in a typical flask (e.g., 250 ml round bottom flask), to a cloudy, and often viscous consistency, such as occurred in Comparative Example 1). Such gelling typically occurs without the use of the additional stabilizing organic groups bound to the amine-functional inorganic nanoparticles.

Functionalizing nanoparticles with amine-functional groups is preferably done by initially functionalizing the particles with stabilizing (typically, non-amine-functional) organic groups using, for example, compounds of the formula A-Q, as can be done by one of skill in the art using conventional techniques. Such organic groups (referred to herein as "stabilizing" organic groups) can be selected to stabilize a plurality of the resultant amine-functional inorganic nanoparticles when dispersed in a liquid (e.g., water, alcohols (e.g., methanol, ethanol, 1-methoxy-2-propanol, or glycols), or combinations thereof) before complexing the amine-functional organic groups with a triorganoborane.

In certain embodiments of the compound of formula A-Q, group A group is a hydrolyzable silyl group of formula —Si(R$^3$)(R$^4$)$_2$ where R$^3$ is a hydrolyzable group and R$^4$ is a hydrolyzable group or a non-hydrolyzable group. In certain embodiments, group Q is a (C3-C16)alkyl group or a (C6-C14)aryl group.

Thus, the amine-functional inorganic nanoparticles that include bound stabilizing organic groups can be made by a method that includes: providing inorganic oxide nanoparticles that include bound stabilizing organic groups selected to stabilize a plurality of the nanoparticles when dispersed in a polar liquid (e.g., water, alcohols (e.g., methanol, ethanol, 1-methoxy-2-propanol, or glycols), or combinations thereof); providing an amine-functional compound (e.g., a compound of the formula A-ZNHR$^1$); and combining the amine-functional compound and inorganic nanoparticles including bound stabilizing organic groups under conditions effective to form the amine-functional inorganic nanoparticles that include bound stabilizing organic groups. Suitable amine-functional compounds (e.g., compounds of the formula A-ZNHR$^1$) for making the amine-functional nanoparticles often include a group A that is a hydrolyzable silyl group of formula —Si(R$^3$)(R$^4$)$_2$ as defined above. Exemplary amine-functional compounds include, but are not limited to, aminoalkyltrialkoxysilanes or aminoaryltrialkoxysilanes such as 3-aminopropyltrimethoxysilane, 3-aminopropyltriethoxysilane, 3-aminopropyldiethoxymethylsilane, 3-aminopropyldimethylethoxysilane, m-aminophenyltrimethoxysilane, p-aminophenyltrimethoxysilane, and 11-aminoundecyltriethoxysilane.

A method of the present disclosure further involves: providing a triorganoborane compound of the formula B(R$^2$)$_3$ wherein each R$^2$ is an organic group bound to the boron atom through a carbon atom; and combining the amine-functional inorganic oxide nanoparticles that include organic groups and the triorganoborane compound under conditions effective to form surface-modified nanoparticles, wherein each surface-modified nanoparticle includes an inorganic core and surface modifying groups as described herein.

In such method, preferably the amount of triorganoborane compound (B(R$^2$)$_3$) used is less than an equivalent amount relative to the number of amine-functional groups on the nanoparticles, at least because excess triorganoborane can be unstable. The formation of the N(H)—B(R$^2$)$_3$ bond, and hence, the formation of amine-triorganoborane complexes bound to the nanoparticles, can be identified, for example, through $^{11}$B NMR spectroscopy.

In certain embodiments, combining the amine-functional inorganic nanoparticles and the triorganoborane compound (B(R$^2$)$_3$) can be done by a method that includes mixing them together in a solvent, which is subsequently removed from the resultant surface-modified nanoparticles that include an inorganic core and surface modifying groups as described herein. Typically, in this method, the solvent is selected from alkanes (e.g., hexane), aromatics (e.g., toluene), ethers (e.g., THF), or combination thereof.

In certain embodiments, combining the amine-functional inorganic nanoparticles and the triorganoborane compound (B(R$^2$)$_3$) can be done by a method that includes: adding the triorganoborane compound in a solvent to dry amine-functional inorganic nanoparticles, such as, for example, by spraying; and agitating the nanoparticles to evaporate the solvent from the resultant surface-modified inorganic nanoparticles that include an inorganic core and surface modifying groups as described herein. Typically, in this method, the solvent is tetrahydrofuran (THF) or hexane.

Combining the amine-functional inorganic nanoparticles and the triorganoborane compound (B(R$^2$)$_3$) can be done in air, or it can be done in an inert atmosphere, such as in a nitrogen atmosphere. Combining the amine-functional inorganic nanoparticles and the triorganoborane compound (B(R$^2$)$_3$) can be done at any temperature, including lower temperatures (e.g., −20° C., −10° C., or 0° C.), room temperature, and higher temperatures (e.g., temperatures as high as the boiling point of the solvent).

The methods described herein are facile and controllable for preparing surface-modified nanoparticle that include an inorganic core and bound —Z—NHR$^1$—B(R$^2$)$_3$ complexes as well as bound -Q stabilizing organic groups. For example, such methods provide a known and predictable amount of bound —Z—NHR$^1$—B(R$^2$)$_3$ complexes. Furthermore, methods described herein avoid gel formation, particularly when using nanoparticles, as defined herein.

In contrast, methods that use simply an amine-functional compound, such as 3-aminopropyl trimethoxysilane, with fumed silica or silica nanoparticles but without the stabilizing organic groups, often result in the formation of a gel (Comparative Example 1 using fumed silica, and Comparative Example 4 with silica nanoparticles). Methods that use an amine-functional compound with fumed silica and with the stabilizing organic groups form a white powder that does not provide an effective free-radical source upon combining with a triorganoborane (Comparative Example 2, Comparative Example 6, and Comparative Example 10). That is, fumed silica (which is not considered to be an inorganic nanoparticle) is not suitable as a core material for the —Z—NHR$^1$—B(R$^2$)$_3$ complexes. When fumed silica was treated with a mixture of an amine-functional compound, such as 3-aminopropyl trimethoxysilane, and a source of a stabilizing group, such as isooctyltrimethoxysilane, that the resulting modified fumed silica does not provide an effective free-radical source upon combining with a triorganoborane, as evidenced by Comparative Examples 9-11, which use the material of Comparative Examples 5-7, which uses the material of Comparative Example 2).

Comparative Examples 1 and 3 use fumed silica with an amine-functional compound, such as 3-aminopropyl trimethoxysilane, as described in U.S. Pat. No. 7,649,068. Comparative Example 1 demonstrates that if the mixture includes a solvent (water), a gel forms. Formation of a gel is undesired. Comparative Example 3 demonstrates that if the mixture does not include a solvent (i.e., the fumed silica is used in the dry state), a material forms that does not provide an effective free-radical source upon combining with a triorganoborane, as evidenced by Comparative Example 12, which uses the material of Comparative Example 8, which uses the material of Comparative Example 3).

Thus, the present disclosure provides a much more controllable method of making triorganoborane-amine functionalized nanoparticles that do not gel and that are an effective source of triorganoborane.

Uses

The surface-modified nanoparticles of the present disclosure have broad application. They can be useful, for example, in filled composites, including highly filled composites, in two-part structural adhesives, and in curable (meth)acrylate-containing compositions.

The surface-modified nanoparticles of the present disclosure can be provided as a dry, solid material. Such dry, solid material is more stable than the free triorganoborane and conventional amine-borane structures, which are typically dissolved in liquids under an inert atmosphere. Furthermore, the solid particles provide a safer means of delivery of the triorganoborane because a significant part of the particle is inorganic.

Alternatively, the nanoparticles of the present disclosure can be provided in a dispersion of a plurality of surface-modified nanoparticles in a liquid. The surface-modified nanoparticles of the present disclosure can be used in a polymerizable composition that includes a polymerizable component (which can be the liquid).

Such dispersion is preferably stable, both physically and chemically. By physically stable, it is meant that such dispersion is transparent or slightly hazy (but not cloudy) in appearance, such that it can be seen through in a typical flask (e.g., 250 ml round bottom flask). By chemically stable, it is meant that the bound triorganoborane-amine complex is stable to, for example, decomposition by or reaction with atmospheric oxygen and/or atmospheric water.

Useful decomplexing agents include isocyanates, acids (including carboxylic acids), and carboxylic acid anhydrides. Useful isocyanates can include, e.g., phenyl isocyanate, toluene diisocyanate, and polyisocyanates such as those available from Bayer MaterialScience, Pittsburgh, Pa., under the trade designations DESMODUR N100 and DESMODUR N3300. Useful acids include mineral acids such as hydrochloric acid and sulfuric acid, carboxylic acids, including mono-, di-, and polycarboxylic acids such as acetic acid, propionic acid, oxalic acid, succinic acid, and maleic acid acrylic acid, and methacrylic acid, and sulfonic acids such as benzenesulfonic acid and toluenesulfonic acid. Useful carboxylic anhydrides include succinic anhydride, malic anhydride, acrylic anhydride, and itaconic anhydride. Useful decomplexing agents are described in, for example, U.S. Pat. No. 5,686,544 (Pocius), WO 97/07171 (Deviny), U.S. Pat. No. 5,872,197 (Deviny), and U.S. Pat. No. 6,812,308 (Deviny et al.). The liberated triorganoborane is capable of initiating the polymerization of the polymerizable component, typically through a free-radical mechanism.

Typically, such polymerizable component includes ethylenically unsaturated monomers, oligomers, as well as polymers having one or more ethylenically unsaturated group. Suitable compounds contain at least one ethylenically unsaturated bond and are capable of undergoing addition polymerization. Such free-radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free-radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free-radically polymerizable compounds can be used if desired.

In certain embodiments, the surface-modified nanoparticles can be incorporated into a dual-cure system. A dual-cure system typically includes two polymerizable components, e.g., a first polymerizable component such as a thermoset component (e.g., a polyurea, a polyurethane or an epoxy thermoset), and a second polymerizable component such as a polymerizable acrylate component. The polymerizable acrylate component can be any polymerizable acrylate component comprising one or more acrylate or methacrylate monomers.

The components of a dual-cure system independently polymerize to form a cured material (e.g., a coating on a substrate). The thermoset component can polymerize to form, for example, a polyurea by the spontaneous reaction of an amine with an isocyanate. The acrylate component can polymerize to form an acrylic homopolymer or copolymer. The acrylic polymer can be crosslinked or not crosslinked. The thermoset and acrylic polymers in the cured material can be chemically bonded to each other (by, for example, including in the composition a compound that is reactive with both the thermoset component and the acrylate component), or they can form an interpenetrating polymer network (IPN), where the components are not chemically bonded to each other.

In one illustrative embodiment, the dual-cure system is a 2-part system that can polymerize to form a polyurea (by spontaneous reaction of a polyamine component and a polyisocyanate component) and a polyacrylate (by polymerization of one or more acrylate monomers). In this embodiment, a first part comprises a polyamine component and the organoborane-amine functionalized nanoparticles, and a second part comprises a polyisocyanate component and one or more acrylate monomers. Optionally, a portion of the polyisocyanate in the second part can serve as a decomplexing agent to liberate the triorganoborane from the triorganoborane-amine functionalized nanoparticle, or the second part can further comprise a decomplexing agent. After the 2-parts are mixed, the polyamine component and the polyisocyanate component can spontaneously react to form a polyurea, and the released triorganoborane can react to initiate polymerization of the one or more acrylate monomers.

Typically, such systems have an advantage over traditional polyurea, polyurethane, epoxy, or acrylate coatings, in that the two curable components provide a way to control or modify physical properties of the cured material, such as hardness and flexibility, by controlling the chemistry of each component.

ILLUSTRATIVE EMBODIMENTS

1. A surface-modified nanoparticle comprising an inorganic core and surface modifying groups, wherein the surface modifying groups comprise at least one triorganoborane-amine complex having the structure —Z—NHR$^1$—B(R$^2$)$_3$ wherein:
   Z is a divalent organic group;
   R$^1$ is H or an organic group; and
   each R$^2$ is independently an organic group bound to the boron atom through a carbon atom.

2. The nanoparticle of embodiment 1 wherein the inorganic core comprises an inorganic oxide core.

3. The nanoparticle of embodiment 1 wherein the inorganic core comprises zirconia, titania, silica, ceria, alumina, iron oxide, vanadia, germanium oxide, zinc oxide, antimony oxide, tin oxide, or alumina-silica.

4. The nanoparticle of embodiment 3 wherein the inorganic oxide core comprises silica, zirconia, or alumina.

5. The nanoparticle of embodiment 4 wherein the inorganic core comprises silica.

6. The nanoparticle of any one of embodiments 1 through 5 wherein Z is a divalent organic group having 1 to 30 carbon atoms.

7. The nanoparticle of any one of embodiments 1 through 6 wherein R$^1$ is H, an alkyl group, an aryl group, a cycloalkyl group, or a combination thereof.

8. The nanoparticle of embodiment 7 wherein R$^1$ is methyl, ethyl, n-propyl, —CH$_2$-phenyl, or —CH$_2$-cyclohexyl.

9. The nanoparticle of any one of embodiments 1 through 8 wherein each R$^2$ is independently an alkyl group, an aryl group, a cycloalkyl group, or a combination thereof.

10. The nanoparticle of any one of embodiments 1 through 9 wherein:
   Z is a divalent organic group having 1 to 30 carbon atoms;
   R$^1$ is H, an alkyl group, or a cycloalkyl group; and
   each R$^2$ is independently an alkyl group, a cycloalkyl group, an aralkyl group, or an alkaryl group.

11. The nanoparticle of embodiment 10 wherein:
   Z is a divalent organic group having 1 to 20 carbon atoms;
   R$^1$ is H or a (C1-C6)alkyl group or a (C4-C8)cycloalkyl group; and
   each R$^2$ is independently a (C1-C20)alkyl group, a (C4-C8)cycloalkyl group, a (C6-C14)ar(C1-C10)alkyl group, or a (C1-C10)alk(C6-C14)aryl group.

12. The nanoparticle of any one of embodiments 1 through 11 wherein each R$^2$ is independently an alkyl group or a cycloalkyl group.

13. The nanoparticle of embodiment 12 wherein:
   Z is a divalent organic group having 1 to 3 carbon atoms;
   R$^1$ is H; and
   each R$^2$ is independently a (C1-C6)alkyl group.

14. The nanoparticle of any one of embodiments 1 through 13 wherein each R$^2$ is the same in the structure —Z—NHR$^1$—B(R$^2$)$_3$.

15. The nanoparticles of any one of embodiments 1 through 14 wherein Z is an alkylene.

16. The nanoparticle of any one of embodiments 1 through 15 wherein the surface modifying groups further comprise amine-functional organic groups not complexed with a triorganoborane.

17. The nanoparticle of any one of embodiments 1 through 16 wherein the surface modifying groups further comprise stabilizing organic groups bound to the nanoparticles.

18. The nanoparticle of embodiment 17 wherein the stabilizing organic groups comprise (C1-C30)organic groups optionally containing catenary oxygen atoms and other functional groups.

19. The nanoparticle of embodiment 18 wherein the stabilizing organic groups comprise a (C3-C16)alkyl group, a (C6-C14)aryl group, or combinations thereof.

20. A dispersion of a plurality of surface-modified nanoparticles of any one of embodiments 1 through 18 in a liquid.

21. The dispersion of embodiment 20 which is stable.

22. The dispersion of embodiment 20 or 21 wherein the liquid comprises polymerizable monomer.

23. A method of making surface-modified nanoparticles, the method comprising:
providing amine-functional inorganic nanoparticles comprising bound stabilizing organic groups selected to stabilize a plurality of the amine-functional inorganic nanoparticles when dispersed in a liquid;
providing a triorganoborane compound of the formula $B(R^2)_3$ wherein each $R^2$ is an organic group bound to the boron atom through a carbon atom; and
combining the amine-functional inorganic nanoparticles and the triorganoborane compound under conditions effective to form surface-modified nanoparticles, wherein each surface-modified nanoparticle comprises an inorganic core and surface modifying groups, wherein the surface modifying groups comprise at least one triorganoborane-amine complex having the structure $-Z-NHR^1-B(R^2)_3$ wherein:
Z is a divalent organic group;
$R^1$ is H or an organic group; and
each $R^2$ is independently an organic group bound to the boron atom through a carbon atom.

24. The method of embodiment 23 wherein providing amine-functional inorganic nanoparticles comprising bound stabilizing organic groups, comprises:
providing inorganic nanoparticles comprising bound stabilizing organic groups selected to stabilize a plurality of the nanoparticles when dispersed in a liquid;
providing an amine-functional compound; and
combining the amine-functional compound and inorganic nanoparticles comprising bound stabilizing organic groups under conditions effective to form amine-functional inorganic nanoparticles comprising bound stabilizing organic groups.

25. The method of embodiment 24 wherein combining the amine-functional compound and inorganic nanoparticles occurs in a solvent selected from water, an alcohol, or a combination thereof.

26. The method of any one of embodiments 23 through 25 wherein combining the amine-functional inorganic nanoparticles and the triorganoborane compound occurs in a solvent, which is subsequently removed from the resultant surface-modified nanoparticles that include an inorganic core and the surface modifying groups.

27. The method of embodiment 26 wherein the solvent is selected from an alkane, an aromatic, an ether, or a combination thereof.

28. The method of any one of embodiments 23 through 25 wherein combining the amine-functional inorganic nanoparticles and the triorganoborane compound comprises:
spraying the triorganoborane compound in a solvent onto dry amine-functional inorganic nanoparticles; and
agitating the nanoparticles to evaporate the solvent to form the resultant surface-modified inorganic oxide nanoparticles comprising an inorganic core and surface modifying groups.

29. The method of embodiment 28 wherein the solvent is THF or hexane.

30. A polymerizable composition comprising a polymerizable component and surface-modified nanoparticles, wherein each surface-modified nanoparticle comprises surface modifying groups, wherein the surface modifying groups comprise at least one triorganoborane-amine complex having the structure $-Z-NHR^1-B(R^2)_3$ wherein:
Z is a divalent organic group;
$R^1$ is H or an organic group; and
each $R^2$ is independently an organic group bound to the boron atom through a carbon atom.

31. The composition of embodiment 30 which is part of a dual-cure system.

32. The composition of embodiment 30 or 31 wherein surface-modified nanoparticle further comprises bound stabilizing organic groups.

33. The composition of embodiment 32 wherein the stabilizing organic groups comprise a (C3-C16)alkyl group, a (C6-C14)aryl group, or combinations thereof.

EXAMPLES

Objects and advantages of this disclosure are further illustrated by the following examples, but the particular materials and amounts thereof recited in these examples, as well as other conditions and details, should not be construed to unduly limit this disclosure.

The following examples are merely for illustrative purposes and are not meant to limit in any way the scope of the appended claims. All parts, percentages, ratios, and the like in the examples are by weight, unless noted otherwise. Unit abbreviations used include h=hours, gm=grams, wt=weight, cm=centimeter. Unless otherwise stated, materials were obtained from Sigma-Aldrich, St. Louis, Mo.

Preparative Example 1

An aqueous dispersion of silica (100 gm; obtained under the trade designation Nalco 2326 from Nalco Company, Naperville, Ill.) was weighed into a 3-neck round bottom flask equipped with a water cooled condenser and a mechanical stirrer. A mixture of isooctyltrimethoxysilane (3.41 gm; obtained from Gelest, Inc., Morrisville, Pa.) and 1-methoxy-2-propanol (100 gm; obtained from Alfa Aesar, Ward Hill, Mass.) was added to the stirring Nalco dispersion. The flask was then placed in an oil bath and was heated at 80° C. for two hours. A mixture of 3-aminopropyltrimethoxysilane (3.41 gm; obtained from Sigma-Aldrich Corp., St. Louis, Mo.) and 1-methoxy-2-propanol (22.1 gm) was then added to the flask. The mixture was stirred at 80° C. overnight. The reaction mixture was then poured into a Pyrex dish, and was dried at 150° C. in a forced air oven to afford the product as a white powder.

Preparative Example 2

An aqueous dispersion of silica (100 gm; obtained under the trade designation Nalco 2327 from Nalco Company, Naperville, Ill.) was weighed into a 3-neck round bottom flask equipped with a water cooled condenser and a mechanical stirrer. A mixture of phenyltrimethoxysilane (1.75 gm; obtained from Sigma-Aldrich Corp., St. Louis, Mo.) and 1-methoxy-2-propanol (about 60 gm) was added to the stirring Nalco dispersion. The flask was then placed in an oil bath and was heated at 80° C. for about 4 hours. A mixture of 3-aminopropyltrimethoxysilane (3.41 gm) and 1-methoxy-2-propanol (about 60 gm) was then added to the flask. The mixture was stirred at 80° C. overnight. The reaction mixture was then poured into a Pyrex dish, and was dried at 150° C. in a forced air oven to afford the product as a white powder.

Preparative Example 3

An aqueous dispersion of silica (500 gm; obtained under the trade designation Nalco 2326 from Nalco Company, Naperville, Ill.) was weighed into a 3-neck round bottom flask equipped with a water cooled condenser and a mechanical stirrer. A mixture of hexadecyltrimethoxysilane (24.36 gm; obtained from Gelest, Inc., Morrisville, Pa.) and a mixture of 20 weight percent methanol in ethanol (about 280 gm) was added to the stirring Nalco dispersion. The flask was then placed in an oil bath and was heated at 80° C. for about 4 hours. A mixture of 3-aminopropyltrimethoxysilane (12.60 gm) and 20 weight percent methanol in ethanol (about 280 gm) was then added to the flask. The mixture was stirred at 80° C. overnight. The reaction mixture was then poured into a Pyrex dish, and was dried at 150° C. in a forced air oven to afford the product as a white powder.

Preparative Example 4

An aqueous dispersion of silica (500 gm; obtained under the trade designation Nalco 2326 from Nalco Company, Naperville, Ill.) was weighed into a 3-neck round bottom flask equipped with a water cooled condenser and a mechanical stirrer. A mixture of isooctyltrimethoxysilane (16.44 gm; obtained from Gelest, Inc., Morrisville, Pa.) and a mixture of 20 weight percent methanol in ethanol (about 280 gm) was added to the stirring Nalco dispersion. The flask was then placed in an oil bath and was heated at 80° C. for about 4 hours. A mixture of N,N-dimethyl-3-aminopropyltrimethoxysilane (14.57 gm) and 20 weight percent methanol in ethanol (about 280 gm) was then added to the flask. The mixture was stirred at 80° C. overnight. The reaction mixture was then poured into a Pyrex dish, and was dried at 150° C. in a forced air oven to afford the product as a white powder.

Preparative Example 5

An aqueous dispersion of silica (100 gm; obtained under the trade designation Nalco 2326 from Nalco Company, Naperville, Ill.) was weighed into a 3-neck round bottom flask equipped with a water cooled condenser and a mechanical stirrer. A mixture of isooctyltrimethoxysilane (3.29 gm; obtained from Gelest, Inc., Morrisville, Pa.) and a mixture of 20 weight percent methanol in ethanol (about 56 gm) was added to the stirring Nalco dispersion. The flask was then placed in an oil bath and was heated at 80° C. for about 4 hours. A mixture of N-phenyl-3-aminopropyltrimethoxysilane (3.59 gm) and 20 weight percent methanol in ethanol (about 56 gm) was then added to the flask. The mixture was stirred at 80° C. overnight. The reaction mixture was then poured into a Pyrex dish, and was dried at 150° C. in a forced air oven to afford the product as a white powder.

Comparative Example 1

Fumed silica (16.6 gm; available under the trade designation AEROSIL 200 from Evonik Degussa Corp., Parsippany, N.J.) and water (83.4 gm) were weighed into a 3-neck round bottom flask equipped with a water cooled condenser and a mechanical stirrer. A mixture of 3-aminopropyltrimethoxysilane (3.41 gm; obtained from Sigma-Aldrich Corp., St. Louis, Mo.) and 1-methoxy-2-propanol (122 gm) was then added to the flask. The viscosity of the mixture rapidly increased, and stirring was impeded. The mixture appeared to form a gel.

Comparative Example 2

Fumed silica (16.6 gm; available under the trade designation AEROSIL 200 from Evonik Degussa Corp., Parsippany, N.J.) and water (83.4 gm) were weighed into a 3-neck round bottom flask equipped with a water cooled condenser and a mechanical stirrer. A mixture of 3-aminopropyltrimethoxysilane (3.41 gm; obtained from Sigma-Aldrich Corp., St. Louis, Mo.), isooctyltrimethoxysilane (3.41 gm; obtained from Gelest, Inc., Morrisville, Pa.) and 1-methoxy-2-propanol (122 gm) was then added to the flask. The flask was then placed in an oil bath and the mixture was stirred and heated at 80° C. overnight. The reaction mixture was then poured into a Pyrex dish, and was dried at 150° C. in a forced air oven to afford the product as a white powder.

Comparative Example 3

Fumed silica (16.6 gm; available under the trade designation AEROSIL 200 from Evonik Degussa Corp., Parsippany, N.J.) was weighed into a 3-neck round bottom flask equipped with a water cooled condenser and a mechanical stirrer. Then 3-aminopropyltrimethoxysilane (3.41 gm; obtained from Sigma-Aldrich Corp., St. Louis, Mo.), was added to the flask containing the AEROSIL 200 in the dry state. The flask was then placed in an oil bath and the mixture was stirred and heated at 80° C. overnight. The reaction mixture was then poured into a Pyrex dish, and was dried at 150° C. in a forced air oven to afford the product as a white powder.

Comparative Example 4

An aqueous dispersion of silica (100 gm; obtained under the trade designation Nalco 2326 from Nalco Company, Naperville, Ill.) was weighed into a 3-neck round bottom flask equipped with a water cooled condenser and a mechanical stirrer. 1-Methoxy-2-propanol (100 gm; obtained from Alfa Aesar, Ward Hill, Mass.) was added to the stirring Nalco dispersion. The flask was then placed in an oil bath and was heated at 80° C. for two hours. A mixture of 3-aminopropyltrimethoxysilane (3.41 gm; obtained from Sigma-Aldrich Corp., St. Louis, Mo.) and 1-methoxy-2-propanol (22.1 gm) was then added to the flask. The viscosity of the mixture rapidly increased, and stirring was impeded. The mixture appeared to form a gel.

Comparative Example 5

A round bottom flask was charged with the product of Comparative Example 2 (1.01 gm) and toluene (approximately 20 mL). After the flask was flushed with nitrogen gas, a 1 molar solution of triethylborane in hexane (0.6 mL) was added to the flask via syringe. The mixture was magnetically stirred for about 1 hour at room temperature. The solvent was removed using a rotary evaporator to afford the product as a white powder.

Comparative Example 6

A round bottom flask was charged with the product of Comparative Example 3 (1.01 gm) and toluene (approximately 20 mL). After the flask was flushed with nitrogen gas, a 1 molar solution of triethylborane in hexane (0.75 mL) was added to the flask via syringe. The mixture was magnetically stirred for about 1 hour at room temperature. The solvent was removed using a rotary evaporator to afford the product as a white powder.

Comparative Example 7

A round bottom flask was charged with the product of Comparative Example 2 (0.5 gm). A solution of 1 molar triethylborane in tetrahydrofuran (0.3 mL) was added to the flask via syringe. The mixture was magnetically stirred for about 1 hour at room temperature to afford the product as a white powder.

Comparative Example 8

A round bottom flask was charged with the product of Comparative Example 3 (0.5 gm). A solution of 1 molar triethylborane in tetrahydrofuran (0.35 mL) was added to the flask via syringe. The mixture was magnetically stirred for about 1 hour at room temperature to afford the product as a white powder.

Example 1

A round bottom flask was charged with the nanoparticle product of Preparative Example 1 (0.5 gm). A solution of 1 molar triethylborane in hexane (0.2 mL) was added to the flask via syringe. The mixture was magnetically stirred for about 1 hour at room temperature to afford the product as a white powder.

Example 2

A round bottom flask was charged with the nanoparticle product of Preparative Example 2 (1.5 gm). A solution of 1 molar triethylborane in hexane (0.22 mL) was added to the flask via syringe. The mixture was magnetically stirred for about 1 hour at room temperature to afford the product as a white powder.

Example 3

A round bottom flask was charged with the nanoparticle product of Preparative Example 3 (0.5 gm). A solution of 1 molar triethylborane in tetrahydrofuran (0.22 mL) was added to the flask via syringe. The mixture was magnetically stirred for about 1 hour at room temperature to afford the product as a white powder.

Example 4

A round bottom flask was charged with the nanoparticle product of Preparative Example 4 (0.25 gm). A solution of 1 molar triethylborane in tetrahydrofuran (0.1 mL) was added to the flask via syringe. The mixture was magnetically stirred for about 1 hour at room temperature to afford the product as a white powder.

Example 5

A round bottom flask was charged with the nanoparticle product of Preparative Example 5 (0.5 gm). A solution of 1 molar triethylborane in tetrahydrofuran (0.25 mL) was added to the flask via syringe. The mixture was magnetically stirred for about 1 hour at room temperature to afford the product as a white powder.

Example 6

A round bottom flask was charged with the nanoparticle product of Preparative Example 1 (10.03 gm) and toluene (approximately 20 mL). After the flask was flushed with nitrogen gas, a 1 molar solution of triethylborane in hexane (7.0 mL) was added to the flask via syringe. The mixture was magnetically stirred for about 1 hour at room temperature. The solvent was removed using a rotary evaporator to afford the product as a white powder.

Example 7

A round bottom flask was charged with the nanoparticle product of Preparative Example 2 (3.03 gm) and hexane (approximately 20 mL). After the flask was flushed with nitrogen gas, a 1 molar solution of triethylborane in hexane (0.45 mL) was added to the flask via syringe. The mixture was magnetically stirred for about 1 hour at room temperature. The solvent was removed using a rotary evaporator to afford the product as a white powder.

Example 8

A round bottom flask was charged with the nanoparticle product of Preparative Example 3 (1.05 gm) and toluene (approximately 20 mL). After the flask was flushed with nitrogen gas, a 1 molar solution of triethylborane in hexane (0.45 mL) was added to the flask via syringe. The mixture was magnetically stirred for about 1 hour at room temperature. The solvent was removed using a rotary evaporator to afford the product as a white powder.

Example 9

A round bottom flask was charged with the nanoparticle product of Preparative Example 4 (0.52 gm) and toluene (approximately 20 mL). After the flask was flushed with nitrogen gas, a 1 molar solution of triethylborane in hexane (0.25 mL) was added to the flask via syringe. The mixture was magnetically stirred for about 1 hour at room temperature. The solvent was removed using a rotary evaporator to afford the product as a white powder.

Example 10

A 200 mL round bottom was charged with 10.03 gm of the amine-functional silica nanoparticles of Preparative Example 1. Toluene (20.5 gm) was then added to the flask. The mixture was magnetically stirred to suspend the nanoparticles. To the stirring suspension of nanoparticles there was added a 1 molar solution of triethylborane in tetrahydrofuran (7.0 mL; 7.0 mmol of triethylborane; obtained from Sigma-Aldrich Corp., St. Louis, Mo.). The calculated stoichiometry was such that there was a calculated molar excess of amino groups relative to the triethylborane. The mixture was allowed to stir at room temperature for approximately 20 minutes, after which time the volatile components were removed using a rotary evaporator. The product was a white free-flowing powder that was stored in the round bottom flask, using a rubber septum to seal the flask.

Example 11

A glass vial was charged with 2.0 g of a solution of 30 weight percent Elvacite 1010 (a methyl methacrylate macromonomer obtained from Lucite International, Cordova, Tenn.) in 1,6-hexanediol diacrylate (SR238; obtained from Sartomer USA, LLC, Exton, Pa.). The nanoparticle products of Example 10 (0.5 g) were added to the vial and were dispersed in the monomer mixture. A second glass vial was charged with 1.0 g of the Elvacite 1010/SR238 mixture, and 0.13 g of glacial acetic acid. The contents of the second vial were transferred in one portion to the first vial using a pipet, and then the resultant composition was mixed by drawing it into the pipet and expelling it into the vial. Within 1 minute the viscosity of the mixture began to increase. After 2 additional minutes, the mixture was not pourable, and after an additional 3 minutes (a total of 6 minutes after mixing), the composition was a polymerized gel Example 12

A glass vial was charged with isobornyl acrylate (1.69 gm; obtained from TCI America, Portland, Oreg.) and the nanoparticle product of Example 10 (0.36 gm). A second glass vial was charged with isobornyl acrylate (0.73 gm) and glacial acetic acid (0.1 gm). The contents of the second vial were transferred in one portion to the first vial using a pipet, and then the resultant composition was mixed by drawing it into the pipet and expelling it into the vial. Within 15 seconds, the mixture became warm and viscous. After an additional 5 seconds (a total of 20 seconds after mixing), the composition was a polymerized gel.

Example 13

A 2-part dual-cure liquid composition capable of forming a polyurea component and a polyacrylate component was prepared. Then the 2 parts were combined and were allowed to react to form the polymers. A first part was prepared by combining in a beaker Clearlink 1000 (5.5 gm; a cycloaliphatic diamine obtained from Dorf Ketal Chemicals, LLC, Stafford, Tex.), Desmophen NH 1420 (20.0 gm; a cycloaliphatic diamine obtained from Bayer MaterialScience, Pittsburgh, Pa.), Ti-Pure R960 (15.0 gm; a surface-modified titanium dioxide obtained from DuPont Co., Wilmington, Del.), and the nanoparticle product of Example 10 (4.0 gm). The combined materials were mixed using a Cowles-type mixer to form a white opaque dispersion. A second part was prepared by combining in a beaker Desmodur XP2410 (17.0 gm; an isocyanurate-based diisocyanate obtained from Bayer MaterialScience), Desmolux D100 (an isocyanurates-based compound having 1 acrylate and 2 isocyanate groups, obtained from Bayer MaterialScience), Desmolux XP2513 (39.0 gm; an isocyanurate-based triacrylate obtained from Bayer MaterialScience), and hexanediol diacrylate (16.0 gm; obtained from Sartomer USA, LLC).

Each part was loaded into separate chambers of a dual-chamber 2:1 dispensing cartridge having a total volume of 50 mL (obtained from Brandywine Materials LLC, Burlington, Mass.). The first part was loaded into the smaller of the two chambers of the cartridge. The entire contents of the cartridge were expelled into a beaker, and the 2 parts were mixed for 40 seconds using a wood tongue depressor. The mixture was coated onto paper release liner at a thickness of 0.635 mm (0.025") using a notched coating bar. The coating formed a cured skin within 20 minutes, and it had enough structural integrity to be peeled from the release liner after 45 minutes.

Example 14

A screw-cap vial was charged with 2-ethylhexyl acrylate (2.0 gm), glacial acetic acid (1 drop) and the product of Example 6 (0.1 gm). The viscosity of the mixture rapidly increased, and within 5 minutes the mixture no longer flowed when the vial was tipped indicating this was an effective polymerization.

Example 15

A screw-cap vial was charged with 2-ethylhexyl acrylate (2.0 gm), glacial acetic acid (1 drop) and the product of Example 7 (0.1 gm). The viscosity of the mixture rapidly increased, and within 5 minutes the mixture no longer flowed when the vial was tipped indicating this was an effective polymerization.

Example 16

A screw-cap vial was charged with 2-ethylhexyl acrylate (2.0 gm), glacial acetic acid (1 drop) and the product of Example 8 (0.1 gm). The viscosity of the mixture rapidly increased, and within 5 minutes the mixture no longer flowed when the vial was tipped indicating this was an effective polymerization.

Example 17

A screw-cap vial was charged with 2-ethylhexyl acrylate (2.0 gm), glacial acetic acid (1 drop) and the product of Example 9 (0.1 gm). The viscosity of the mixture rapidly increased, and within 5 minutes the mixture no longer flowed when the vial was tipped indicating this was an effective polymerization.

Example 18

A screw-cap vial was charged with 2-ethylhexyl acrylate (2.0 gm), glacial acetic acid (1 drop) and the product of Example 1 (0.1 gm). The viscosity of the mixture rapidly increased, and within 5 minutes the mixture no longer flowed when the vial was tipped indicating this was an effective polymerization.

Example 19

A screw-cap vial was charged with 2-ethylhexyl acrylate (2.0 gm), glacial acetic acid (1 drop) and the product of Example 2 (0.1 gm). The viscosity of the mixture rapidly increased, and within 5 minutes the mixture no longer flowed when the vial was tipped indicating this was an effective polymerization.

Example 20

A screw-cap vial was charged with 2-ethylhexyl acrylate (2.0 gm), glacial acetic acid (1 drop) and the product of Example 3 (0.1 gm). The viscosity of the mixture rapidly increased, and within 5 minutes the mixture no longer flowed when the vial was tipped indicating this was an effective polymerization.

Example 21

A screw-cap vial was charged with 2-ethylhexyl acrylate (2.0 gm), glacial acetic acid (1 drop) and the product of Example 4 (0.1 gm). The viscosity of the mixture rapidly increased, and within 5 minutes the mixture no longer flowed when the vial was tipped indicating this was an effective polymerization.

Example 22

A screw-cap vial was charged with 2-ethylhexyl acrylate (2.0 gm), glacial acetic acid (1 drop) and the product of Example 5 (0.1 gm). The viscosity of the mixture rapidly increased, and within 5 minutes the mixture no longer flowed when the vial was tipped indicating this was an effective polymerization.

Comparative Example 9

A screw-cap vial was charged with 2-ethylhexyl acrylate (2.0 gm), glacial acetic acid (1 drop) and the product of Comparative Example 5 (0.1 gm). The viscosity of the mixture did not increase over 15 minutes indicating this was not an effective polymerization.

Comparative Example 10

A screw-cap vial was charged with 2-ethylhexyl acrylate (2.0 gm), glacial acetic acid (1 drop) and the product of Comparative Example 6 (0.1 gm). The viscosity of the mixture did not increase over 15 minutes indicating this was not an effective polymerization.

Comparative Example 11

A screw-cap vial was charged with 2-ethylhexyl acrylate (2.0 gm), glacial acetic acid (1 drop) and the product of Comparative Example 7 (0.1 gm). The viscosity of the mixture did not increase over 15 minutes indicating this was not an effective polymerization.

Comparative Example 12

A screw-cap vial was charged with 2-ethylhexyl acrylate (2.0 gm), glacial acetic acid (1 drop) and the product of Comparative Example 8 (0.1 gm). The viscosity of the mixture did not increase over 15 minutes indicating this was not an effective polymerization.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A surface-modified nanoparticle comprising an inorganic core and surface modifying groups, wherein the surface modifying groups comprise at least one triorganoborane-amine complex having the structure —Z—NHR$^1$—B(R$^2$)$_3$ wherein:
   Z is a divalent organic group;
   R$^1$ is H or an organic group; and
   each R$^2$ is independently an organic group bound to the boron atom through a carbon atom; and
   wherein the surface modifying groups further comprise non-amine functional stabilizing organic groups bound to the nanoparticles.

2. The nanoparticle of claim 1 wherein the inorganic core comprises an inorganic oxide core.

3. The nanoparticle of claim 1 wherein:
   Z is a divalent organic group having 1 to 30 carbon atoms;
   R$^1$ is H, an alkyl group, or a cycloalkyl group; and
   each R$^2$ is independently an alkyl group, a cycloalkyl group, an aralkyl group, or an alkaryl group.

4. The nanoparticle of claim 3 wherein:
   Z is a divalent organic group having 1 to 20 carbon atoms;
   R$^1$ is H or a (C1-C6)alkyl group or a (C4-C8)cycloalkyl group; and
   each R$^2$ is independently a (C1-C20)alkyl group, a (C4-C8)cycloalkyl group, a (C6-C14)ar(C1-C10)alkyl group, or a (C1-C10)alk(C6-C14)aryl group.

5. The nanoparticle of claim 4 wherein:
   Z is a divalent organic group having 1 to 3 carbon atoms;
   R$^1$ is H; and
   each R$^2$ is independently a (C1-C6)alkyl group.

6. The nanoparticle of claim 1 wherein each R$^2$ is the same in the structure —Z—NHR$^1$—B(R$^2$)$_3$.

7. The nanoparticle of claim 1 wherein the surface modifying groups further comprise amine-functional organic groups not complexed with a triorganoborane.

8. The nanoparticle of claim 1 wherein the stabilizing organic group comprises a (C3-C16)alkyl group, a (C6-C14)aryl group, or combinations thereof.

9. A dispersion of a plurality of surface-modified nanoparticles of claim 1 in a liquid.

10. The nanoparticle of claim 1 wherein the inorganic core comprises a particle size of at least 5 nanometers.

11. The nanoparticle of claim 1 wherein the inorganic core comprises a particle size of at least 1 nanometer and no greater than 100 nanometers.

12. The nanoparticle of claim 1 wherein the nanoparticle is provided in a dispersion of a plurality of surface-modified nanoparticles in a liquid.

13. A method of making surface-modified nanoparticles, the method comprising:
   providing amine-functional inorganic nanoparticles comprising bound stabilizing organic groups selected to stabilize a plurality of the amine-functional inorganic nanoparticles when dispersed in a liquid; wherein providing amine-functional inorganic nanoparticles comprising bound stabilizing organic groups, comprises:
   providing inorganic nanoparticles comprising bound stabilizing organic groups selected to stabilize a plurality of the nanoparticles when dispersed in a liquid;
   providing an amine-functional compound; and
   combining the amine-functional compound and inorganic nanoparticles comprising bound stabilizing organic groups under conditions effective to form amine-functional inorganic nanoparticles comprising bound stabilizing organic groups;

providing a triorganoborane compound of the formula $B(R^2)_3$ wherein each $R^2$ is an organic group bound to the boron atom through a carbon atom; and combining the amine-functional inorganic nanoparticles and the triorganoborane compound under conditions effective to form surface-modified nanoparticles, wherein each surface-modified nanoparticle comprises an inorganic core and surface modifying groups, wherein the surface modifying groups comprise at least one triorganoborane-amine complex having the structure —Z—NHR$^1$—B(R$^2$)$_3$ wherein:

Z is a divalent organic group;

R$^1$ is H or an organic group; and each R$^2$ is independently an organic group bound to the boron atom through a carbon atom, and wherein the surface modifying groups further comprise non-amine functional stabilizing organic groups bound to the nanoparticles.

14. The method of claim 13 wherein combining the amine-functional compound and inorganic nanoparticles occurs in a solvent selected from water, an alcohol, or a combination thereof.

15. The method of claim 13 wherein combining the amine-functional inorganic nanoparticles and the triorganoborane compound occurs by mixing them in a solvent, which is subsequently removed from the resultant surface-modified nanoparticles that include an inorganic core and the surface modifying groups.

16. A polymerizable composition comprising a polymerizable component and surface-modified nanoparticles, wherein each surface-modified nanoparticle comprises an inorganic core and surface modifying groups, wherein the surface modifying groups comprise at least one triorganoborane-amine complex having the structure —Z—NHR$^1$—B(R$^2$)$_3$ wherein:

Z is a divalent organic group;

R$^1$ is H or an organic group; and each R$^2$ is independently an organic group bound to the boron atom through a carbon atom.

17. The polymerizable composition of claim 16 which is part of a dual-cure system.

* * * * *

UNITED STATES PATENT AND TRADEMARK OFFICE
CERTIFICATE OF CORRECTION

PATENT NO. : 9,908,904 B2
APPLICATION NO. : 14/652462
DATED : March 6, 2018
INVENTOR(S) : James Garbe Page 1 of 1

It is certified that error appears in the above-identified patent and that said Letters Patent is hereby corrected as shown below:

In the Specification

Column 1,
Line 30, delete "$R^1$" and insert -- R' --, therefor.

Column 3,
Line 21, delete "include" and insert -- include, --, therefor.
Line 35, delete "aromatic," and insert -- aromatic. --, therefor.
Line 37, delete "an" and insert -- aryl --, therefor.

Signed and Sealed this
Seventeenth Day of April, 2018

Andrei Iancu
*Director of the United States Patent and Trademark Office*